|| # United States Patent [19]

Wright

[11] Patent Number: 4,542,542
[45] Date of Patent: Sep. 24, 1985

[54] CORRECTION OF DEFECTS IN THE EYE AND COMPOSITIONS THEREFOR

[75] Inventor: George M. Wright, Mission Viejo, Calif.

[73] Assignee: Innovative Surgical Products, Inc., Santa Ana, Calif.

[21] Appl. No.: 515,816

[22] Filed: Jul. 21, 1983

[51] Int. Cl.$^4$ ............................ A61F 1/16; A61F 1/24
[52] U.S. Cl. ........................................................ 623/6
[58] Field of Search .............................. 3/13; 128/1 R

[56] References Cited

U.S. PATENT DOCUMENTS

| | | | |
|---|---|---|---|
| 3,228,741 | 1/1966 | Becker | 3/13 |
| 3,589,363 | 6/1971 | Banko | 128/276 |
| 3,996,935 | 12/1976 | Banko | 3/13 X |
| 4,002,169 | 1/1977 | Cupler, II | 3/13 UX |
| 4,191,176 | 3/1980 | Spinn et al. | 128/1 R |

OTHER PUBLICATIONS

"Experiments in Refilling the Lens", Julius Kessler, M.D., Archives of Ophthalmology, vol. 71, Mar., 1964.
"Refilling the Rabbit Lens", Julius Kessler, M.D., Archives of Ophthalmology, vol. 76, Oct., 1966.

Primary Examiner—Richard J. Apley
Assistant Examiner—James Prizant
Attorney, Agent, or Firm—Knobbe, Martens, Olson & Bear

[57] ABSTRACT

In the replacement of the lens of an eye, the lens is removed from its natural capsule to leave the capsule intact and a curable polymer composition is injected into the lens capsule where the composition cures to form in sitre a solid, synthetic lens which is optically clear and allows the eye to function.

3 Claims, 4 Drawing Figures

CORRECTION OF DEFECTS IN THE EYE AND COMPOSITIONS THEREFOR

BACKGROUND OF THE INVENTION

This invention is concerned with the treatment of defects in the eye, particularly with the replacement of diseased or otherwise defective lenses, and compositions therefor.

Surgery on the eye is becoming more commonplace and sophisticated as new techniques and devices are developed to combat impaired sight or even blindness. One such field is the replacement of the lens in the eye which can be necessitated, for example, by cataract development which opacifies the lens.

The structure of a human lens is somewhat like an onion in that it comprises a layered body having a central, densely packed nucleus surrounded by layers of less closely packed fibers which form the lens cortex at the outermost layers. This lens body is encased in a transparent membrane, called the lens capsule, whose part facing forwards in the eye is known as the anterior capsule and whose part facing rearwards in the eye is known as the posterior capsule. This structure is connected by an annulus of zonular fibers to the ciliary body whose muscular flexing focuses the lens. The anterior capsule is located behind the iris and the posterior capsule is in contact with the vitreous membrane which retains the vitreous fluid in the eyeball.

In the lens extraction procedures first developed, the lens and capsule were removed together in an intracapsular technique by means of forceps or suction. This procedure is extremely traumatic to the delicate organ and, at that time, the patient thereafter had to wear spectacles with extremely powerful and thick lenses to compensate for the lack of a natural lens in his eye. Such spectacles are unsightly, inconvenient and unsatisfactory. More recently, a less traumatic technique has been developed in which the lens is first particulated and removed from the lens capsule by instruments causing less trauma. Then either the whole capsule is removed or, in an extracapsular procedure appropriate in young people whose posterior capsule and vitreous membrane are difficult to separate, only the anterior capsule is removed and the posterior capsule is left in place. In such procedures a probe is inserted into the lens, which has at its tip means for destroying the lens. Such means include ultrasonic or mechanical devices. For example, U.S. Pat. No. 3,589,363 to Banko et al. and U.S. Pat. No. 4,063,557 to Wuchinich et al. disclose ultrasonic probes which disintegrate the lens by the application of high frequency vibrations to the lens. The probes are provided with passages for aspirating the surgical site and for applying suction there to remove the lens fragments dispersed in the irrigation liquid. U.S. Pat. No. 3,996,935 to Banko discloses a probe having jaws for gradually cutting up the lens and having aspiration and irrigation passages. Alternatively, the lens can be digested or dissolved, for example by enzyme action as disclosed in U.S. Pat. Nos. 4,078,564 and 4,191,176 to Spina et al., and the lens residue removed by conventional aspiration and irrigation techniques or other, conventional mechanical means.

Upon removal of the body of the lens the problem is how to compensate for the lost lens without resorting to spectacles with massive lenses. Banko in U.S. Pat. No. 3,996,935, referred to above, mentions that a highly viscous liquid may be injected into the vacant lens capsule and claims that spectacles or contact lenses are not then required. Culper in U.S. Pat. No. 4,002,169 and Russian Pat. No. 570,363 disclose filling the lens capsule with a silicone. But there is no indication in these patents as to the nature of that liquid nor how precisely the liquid should be chosen. More realistically, modern surgical practice provides in place of the removed, natural lens a synthetic implant: an intraocular lens.

This procedure and various implant devices are now well known and may be used in either the intra or extracapsular procedures mentioned above. The lens implant is placed in the eye, either in the anterior chamber in front of the iris or in the posterior chamber behind the iris, and attached to the scleral spur, ciliary suclus or capsular bag with the lens element in alignment with the pupil. The implant lens typically comprises a central lens element made of a clear, plastics material such as an acrylic polymer (as in U.S. Pat. No. 3,807,398 to Grucza) or sometimes a silicone polymer (as in U.S. Pat. No. 4,198,131 to Birdsall et al. and U.S. Pat. No. 4,206,518 to Jardan et al.). This central lens element is provided with peripheral projections for anchoring the implant in place in the eye. There are many known designs for intraocular lenses; examples of some of such devices besides those mentioned above include those shown in U.S. Pat. Nos. 4,159,546, 4,110,848, 4,174,543 and 4,092,743.

However the intraocular lens implant still suffers from a number of disadvantages. The surgical procedure is extensive, traumatic and very delicate. The implant is rigid and therefore not focusable and its fixation points and hard surfaces frequently cause irritation or even rejection, which requires further treatment. Further, the implant is liable to become displaced by shock or vibration resulting from relatively normal patient behavior so that the patient's activities can be curtailed after implant surgery. What is needed is a radically new approach that overcomes these deficiencies and yet offers a viable alternative to the intraocular lens implant.

We have now found such an alternative which involves a less traumatic and faster surgical procedure than hitherto used in this field and which reduces the risk of infection and provides a lens more like the original, natural lens and which is nontoxic, relatively soft and may be focusable.

SUMMARY OF THE INVENTION

According to this invention there is provided a method of replacing in vivo the natural lens or a previously inserted synthetic lens in the eye which comprises removing that lens from the lens capsule and injecting into said capsule a polymeric composition which cures in the eye to an optically clear, gel-like material which allows the eye to function.

Thus this method maintains the lens capsule intact and uses it as a mold to reactively form a synthetic lens in situ in the eye. The synthetic lens composition before placement in the capsular bag is mobile, i.e. of a consistency such that it can be injected into the capsule where it undergoes a physical change due to a curing action which solidifies the composition. The resultant lens is resilient, self-supportable and of a non-pourable consistency so that it conforms to the shape of the lens capsule and holds its shape therein. Thus the lens in this invention is to be distinguished from a silicone filled capsule, for example, which may sag rather than conform to the desired shape.

The invention also provided a process for forming a lens for an eye which comprises making an incision in the capsule which normally surrounds the natural lens, said incision having a maximum dimension which is less than one-half of the maximum dimension of the natural lens. The material of an artificial lens is then introduced through the incision into the capsule, the artificial lens having a maximum dimension at least twice that of the maximum dimension of the incision.

In another aspect of this invention, there is provided a composition suitable for use in such a method. This composition is a sterilizable and injectable, silicone composition which is curable at body temperature in the eye to form an optically clear material which remains so in the presence of physiological fluids, especially aqueous fluids. The cured composition is also low in bleedable material, i.e. low molecular weight species, which can generate opacity by interaction with cells and the lens environment in the eye or cause phase separation in the cured material. Preferably, the synthetic lens of this invention has approximately the same refractive index as the natural lens it replaces.

The lens-forming composition of the invention preferably comprises (a) a crosslinkable organosiloxane polymer component; (b) a crosslinking component; and (c) an effective amount of catalyst which promotes the crosslinking reaction between components (a) and (b). This composition may be supplied in the form of at least two vessels which separate components (b) and (c) into different vessels. For example, one vessel contains all of crosslinking component (b), optionally in admixture with a portion of polymer component (a); and another vessel contains catalyst component (c) in admixture with some or all of polymer component (a).

DETAILED DESCRIPTION OF THE PREFERRED EMBODIMENT

Figure 1:
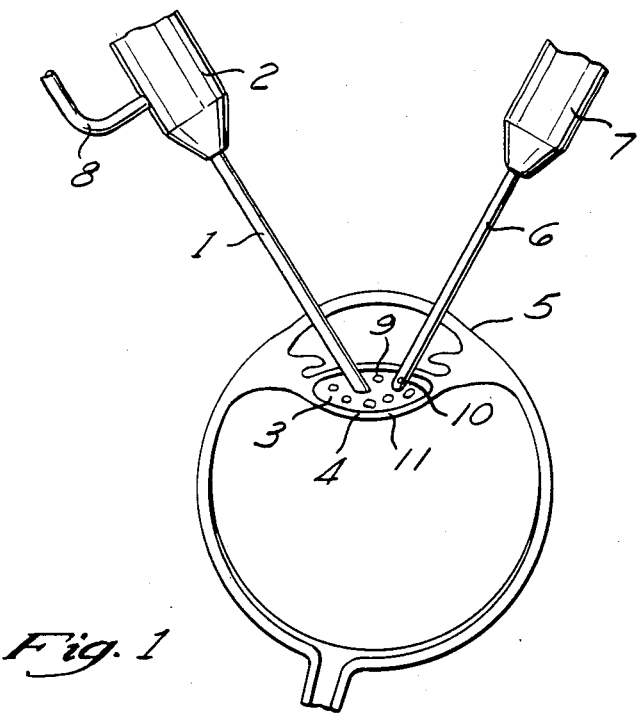
FIG. 1 is a schematic drawing illustrating a known technique for removing the nucleus of the natural lens in preparation for introduction of the synthetic lens in accordance with this invention.

A preliminary step in the method of this invention is the removal of the defective natural lens. The nucleus of the lens is destroyed and removed in any known manner which leaves the lens capsule intact and without the lens. Any of such techniques mentioned above may be used, using the instruments described. Thus the lens may be fragmented by an ultrasonic device as disclosed in U.S. Pat. Nos. 3,589,363 and 4,063,557 or a mechanical device as disclosed in U.S. Pat. No. 3,996,935, the disclosures of these patents being incorporated herein by reference. Preferably an ultrasonic technique, as illustrated in FIG. 1, is used. Referring to that Figure, the needle 1 of an ultrasonic fragmentation device 2 is inserted into the nucleus 3 of the natural lens 4 through the corneal limbus 5. Similarly, the needle 6 of an aspirating device 7, optionally including cutting means (not shown) is inserted into lens nucleus 3. Needles 1 and 6 may be inserted in positions diametrically opposed across the eye, as shown in FIG. 1, or they may be inserted adjacent one another. Fragmentation device 2 is typically provided with a conduit 8 for supplying irrigation fluid such as sterile saline to the needle 1 of device 2. Ultrasonic energy transmitted to a vibrator element (not shown) at the tip of needle 1 breaks up the lens nucleus 3 into fragments 9 which become dispersed in the irrigation fluid and are transported thereby and withdrawn through an orifice 10 in the tip of needle 6 of the aspirating device 7. Device 7 can be simply a means of removing the lens debris or it can also be a cutting tool for breaking up the lens nucleus 3. The use of separate ultrasonic and aspiration devices allows more precision and control of the operation. However, devices 2 and 7 can be incorporated in a single ultrasonic aspiration/irrigation device such as is disclosed in U.S. Pat. Nos. 3,589,363 and 4,063,557 above, with the advantage that only one, rather than two incisions need be made.

Desirably the ultrasonic and aspiration devices 2 and 7 are connected to a fluid control system (not shown) of known type. Such systems are well known in the art and control the flow of fluids at the operating site such that the inflow of irrigation fluid and the outflow of that fluid and entrained surgical debris under aspiration is maintained at as constant a pressure as possible. It is important in removing the lens that the flow control system maintains sufficient pressure in the lens capsule to prevent the capsule collapsing as the lens is removed. Suitable control systems are, for example, disclosed in U.S. Pat. Nos. 3,812,855, 3,920,014, 4,007,742, 4,019,514, and the appropriate disclosures of these patents are incorporated herein by reference.

When the lens capsular bag 11 is emptied of lens nucleus 3, the interior surface of capsule 11 is cleaned of the lens cortex (not shown) and is then ready to accept formation therein of the synthetic lens according to the procedure of this invention.

A polymer composition (as will be described in greater detail hereafter) is prepared comprising silicone prepolymer, crosslinker and curing catalyst. These components are thoroughly mixed together for injection into the lens-free capsule. The composition may be formed in a syringe for direct or indirect injection into the patient's lens capsule. However a more thorough mixing technique uses multiple syringes for mixing in the general manner shown in FIG. 2. In that Figure there is shown three syringes 12, 13 and 14 connected to a four port valve 15. Syringe 12 is loaded with some of crosslinkable silicone polymer component (a), usually about 50% of that component, and all of crosslinking component (b). Syringe 13 is loaded with the remainder of polymer component (a) and all of catalyst component (c). Syringe 14 is initially empty and is preferably sufficiently large to accept the contents of both of syringes 12 and 13.

Figure 2:
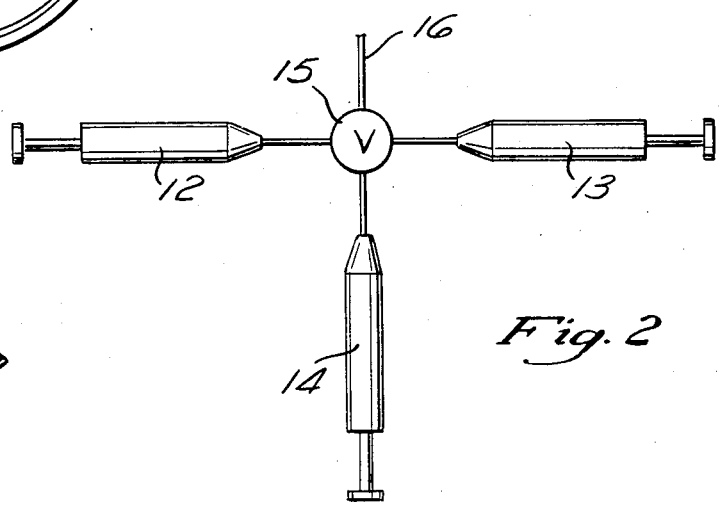
FIG. 2 is a schematic drawing illustrating a means of mixing the components of the curable lens composition of this invention.

Valve 15 is manipulated to allow some of the contents of syringe 12 to be injected into syringe 14 simultaneously with some of the contents of syringe 13. Thus by injection from syringes 12 and 13 the lens composition becomes mixed in syringe 14. Alternatively, some material from syringe 12 may first be injected into syringe 14 and then some material from syringe 13 may be injected into syringe 14 and so on in alternating fashion, however the amounts from each of syringes 12 and 13 should be sufficiently small so as to allow reasonably efficient mixing in syringe 14. When all, or substantially all, the material has been transferred from syringes 12 and 13 to syringe 14, further mixing may be achieved by repeatedly transferring material from syringe 14 to one or both of syringes 12 and 13 or to an additional syringe (not shown) connected to the fourth port 16 of valve 15. In any event, it will be apparent that material can be passed from one syringe to another in any desired manner to achieve thorough mixing. While the above-described initial partitioning of the curable composition into two syringes is preferred, it will also be apparent that other arrangements with two or more syringes could be used or the composition could be placed directly in one syringe. Referring again to FIG. 2, when sufficient mixing has been achieved and thoroughly mixed composition has been injected into syringe 14, that syringe may be disconnected from the mixing system shown and used to inject the curable lens composition directly or indirectly into the patient's lens capsule. Alternatively, mixed material from syringe 14 can be injected directly or indirectly to the patient via valve 15 and port 16. A kit of syringes, optionally with valve and suitable connectors may be supplied for convenience to the physician in presealed, sterilized packaging either connected as shown in FIG. 2 or in two or more separate packages of syringes, preferably with appropriate connectors and valve 15. Most preferably, syringes are supplied prefilled with components of the curable lens composition appropriately separated as described above to prevent premature reaction.

Figure 3:
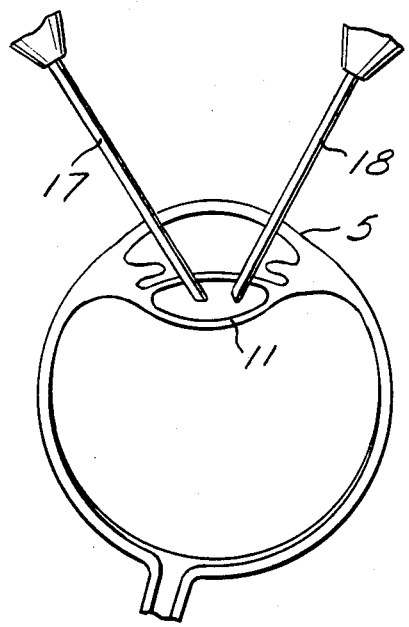
FIG. 3 is a schematic drawing illustrating the formation in the lens capsule of the synthetic lens in the procedure of this invention.

Referring to FIG. 3, after destruction and removal of the natural lens needles 17 and 18 are provided extending into the lens capsule 11 which is free of its lens. Needle 17 has multiple passageways (not shown), one of which conducts sterile irrigation fluid into the lens capsule 11 to maintain its shape in the absence of a lens and to prevent it from collapsing. Excess fluid is removed from the capsule 11 via needle 18 which is connected to an aspiration device (not shown). Another passage in needle 17 is for conducting the synthetic lens composition into capsule 11, although clearly a separate needle could be used for this purpose. In order to minimize the number of insertion and operation time, it is preferred that needle 17 corresponds to needle 1 in FIG. 1 and needle 18 corresponds to needle 6 in FIG. 1. Thus the devices 2 and 7 in FIG. 1 can remain in place throughout the operation, device 1 providing irrigation throughout, ultrasonic energy initially and the lens composition towards the end of the operation, and device 7 providing aspiration throughout. The synthetic, curable lens composition of this invention is therefore conducted into needle 17. The supply of irrigation fluid is halted and the lens composition is gradually introduced into capsule 11 displacing the fluid there which, together with any air bubbles, is withdrawn from capsule 11 through needle 18. Sufficient lens composition is injected into capsule 11 to substantially fill it and then all incisions into the capsule are sealed. This may be achieved by heating the tips of needles 17 and 18 from a separate power source (not shown) to cause localized curing and solidification of the lens composition to plug the incisions in capsule 11 caused by needles 17 and 18. In addition or alternatively, the incisions may be cauterized by the hot needles. Alternatively discrete plugs may be introduced to block the incisions. In the procedure of this invention, all incisions are through the periphery of the lens capsule so that they are out of the line of sight.

The amount of curable lens composition inserted into the lens capsule and the refractive index of the cured composition may be selected to produce a lens which is substantially the same as the extracted natural lens when healthy or these parameters may be selected to correct optical deficiencies previously present in the natural lens. Thus by appropriate manipulation of these parameters, a lens of different power than the original may be created and after the surgical procedure the need for spectacles or contact lenses can be avoided.

Figure 4:
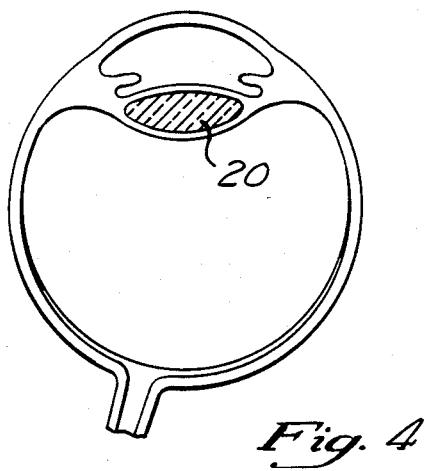
FIG. 4 is a schematic drawing illustrating the lens of this invention in place in the eye and after surgery with the surgical instruments removed.

After withdrawal of the instruments from the eye and sealing of all incisions, the curable composition is left in the lens capsule and allowed to cure and the patient avoids substantial movement until the composition will hold its shape in the eye. The lens composition of this invention cures in situ in the eye to form a new, synthetic lens 19 as shown in FIG. 4. The lens composition of this invention possesses a combination of unique properties. The composition is nontoxic and cures at body temperature, about 37° C., without external curing aids. Moreover, the composition is free of particulate filler material to produce a lens which is optically clear and the cured product is low in migrateable or bleedable species so that phase separation of components or migration thereof is prevented so that the cured lens remains clear, especially in the presence of physiological fluids such as aqueous fluids which cause opacity in silicone compositions. Thus, in marked contrast to silicone oils, the compositions of this invention are curable, will hold their shape upon cure and are low in extractable silicones. That is to say that upon prolonged solvent extraction, less than 65% by weight of the cured product can be extracted by the solvent, preferably less than 40–50%, more preferably less than 30% and most preferably less than 10%.

Preferably, the catalysed composition crosslinks at body temperature to a point at which it will hold its shape in about 2 to 10 hours, preferably about 2 to 3 hours. Full cure is preferably obtained in about 1 to 24 days after injection, more preferably in about 1 to 3 days. In order to allow sufficient time for mixing of the composition and injection, the composition preferably will remain injectable after mixture for about 1 to 2 hours.

As mentioned above, the novel composition for use in the method of this invention comprises (a) a crosslinkable organosiloxane component; (b) a crosslinking component; and (c) a crosslinking catalyst which promotes gelation of the composition at body temperature. These components are selected to provide a cured composition which is optically clear and does not turn cloudy in the eye. Thus the components are selected to provide a cured synthetic lens having a refractive index of from about 1.3 to 1.6, preferably about 1.4 and a density of from about 0.90 to 1.4.

Component (a) preferably comprises a crosslinkable, high molecular weight, organosiloxane polymer substantially free of hydrophilic groups, i.e. polar and ionic groups which could generate opacity in the lens material in the presence of water. Conveniently, such groups are avoided by polymerizing monomers in the presence of acid catalyst.

Component (b) preferably comprises a high molecular weight polyorganosiloxane containing cross linkable groups reactive with the crosslinkable groups of component (a).

Component (c) preferably comprises a platinum catalyst which promotes the crosslinking reaction between components (a) and (b).

In preferred embodiments, and considering these components in turn, component (a) is predominantly composed of material having the average formula:

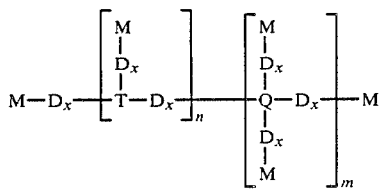
(I)

more preferably:

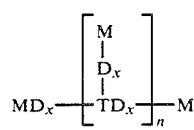
(II)

wherein

M is a monofunctional, silicon-containing, chain-capping residue which is free of crosslinkable groups;

D is a difunctional, siloxane monomer unit;

T is a trifunctional siloxane monomer unit;

Q is a tetrafunctional siloxane monomer unit;

m and n are average numbers whose combined total is preferably from about 2 to 1,000, more preferably from about 10 to 300, and, in Formula II where m=0, n alone has these values; the degree of polymerization of the materials of Formula (I) and (II) is preferably from about 100 to 20,000, more preferably from about 200 to 5,000. The value of the degree of polymerization together with the values of m and n will determine appropriate values of x, as will be apparent to those skilled in the art.

The M, D, T and Q units can be derived from appropriate siloxanes or less preferably, from the hydrolysis of corresponding precursor silanes, usually chlorosilanes.

It will be appreciated by those skilled in the art that these monomers can react together in many different ways and permutations so that the resultant polymer will be a complex mixture of reaction products. Care must be taken to avoid the combination of water and high temperature which may cause excessive branching and subsequent gellation in the reaction flask. Conditions are chosen, however, so that a high proportion of these products have a formula of the type shown above in Formula I and II. Thus these formula are an average representation of a variety of individual polymer molecules that will be present in the polymer product. It will be appreciated that the monomer units in the polymers will be arranged in a substantially random manner. It will also be appreciated that in the formula, some of the side chains could contain T or Q units, causing sub-branching in a complex structure.

The monofunctional residues M are preferably incorporated using a polydiorganosiloxane chain end blocker of the general formula:

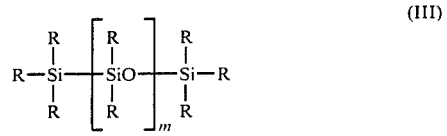
(III)

Wherein the R radicals are the same or different radicals selected from: alkyl, aryl, alkaryl, and aralkyl, said radicals optionally being substituted with functional groups which do not take part in the crosslinking reaction and do not detract from the desired properties of the lens material. Preferably R is $C_1$–$C_{18}$ alkyl, more preferably $C_1$–$C_6$ alkyl, 3-trifluoropropyl or phenyl. Methyl groups throughout, optionally with some phenyl groups, are particularly preferred for the ease of obtaining appropriate starting materials.

m is an average number up to about 30, so that when the R groups are all methyl groups, the compound typically has a number average molecular weight of about 2000.

The difunctional residues, D, are preferably provided by a mixture of at least two monomer sources: (1), in relatively high proportion with respect to the other, and being free of crosslinkable groups and therefore serving as a chain extender, (2) the other, in relatively small proportion, containing the crosslinkable groups. Thus these residues are typically provided by compounds (1) of the general formula:

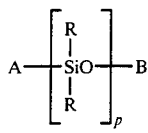
(IV)

wherein R are the same or different radicals and are as defined in Formula III above; said compound having a linear or cyclic structure;

when the compound has a linear structure;
A being

wherein R is as defined above; and
B being

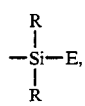

wherein R is as defined above and
E is chloro, methoxy, ethoxy, acetoxy or preferably, hydroxy;
A and B being chemical bonds joined together when the compound has a cyclic structure; and
wherein p is 3 to 8 when the compound is cyclic or 1 to 200 when the compound is linear;
and compounds (2) of the general formula:

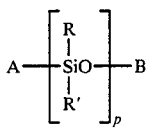
(V)

Wherein A, B, R and p are as defined above and R' is H or an alkenyl group such as vinyl or allyl. Preferably R' is vinyl.

The relative proportions of compounds of categories (1) and (2) is such that there are not so many crosslinkable R' groups present as to result in a brittle composition when cured but sufficient to provide a composition which will hold its shape and cure under the temperature and time conditions mentioned above. Preferably, there are up to about 50 R' groups per molecule if Formula I or II, more preferably about 10. In general, the maximum number of R' groups in Formula I or II is 1 for each branch site or equivalent in the side chains, although, as will be recognized by those skilled in the art, the crosslinking can be controlled when more reactive groups are present in polymer (a) if less crosslinker (b) is used.

The trifunctional residues, T, are preferably provided by reactive silicon compounds which generate branching sites on the polymer backbone. Preferably, this compound has the general formula:

(VI)

wherein $R^2$ is R or R' and wherein R and R' are as defined above and W, Y and Z are the same or different substituents which in the formation of polymer of Formula I or II are converted into volatile or otherwise readily removable by-products and which do not interfere with the desired properties of the final product or with the reactants used to form that product and its components. Preferably W, Y and Z are the same substituents and are $C_1$–$C_6$ alkoxy or acetoxy or chloro or hydroxy. Examples of compounds of Formula VI include: $(CH_3(H)SiO)_4$; $CH_3Si(OOCR^3)_3$, where $R^3$ is methyl, ethyl or propyl; $CH_2=CHSiOR$ and $RSiCl_3$, where R is as defined above.

The tetrafunctional residues, Q, are preferably provided by a reactive silicon compound which is similar to the trifunctional compound. Thus the tetrafunctional compound has the formula:

(VII)

wherein W, X, Y and Z are the same or different and are $C_1$–$C_6$ alkoxy, acetoxy, chloro or hydroxy. Examples of compounds of Formula VII include $Si(OR^3)_4$ where $R^3$ is as defined above; $Si(OOCR^3)_4$ wherein $R^3$ is as defined above.

These mono-, di-, tri- and, optionally, tetrafunctional compounds are reacted in the presence of an acid catalyst to form component (a), a complex liquid polymer. The catalyst may be a mineral acid such as sulfuric acid or an acid ion exchange resin such as Amberlyst 15 supplied by Rohm and Haas Company, Philadelphia and purified if necessary. More preferably, the catalyst is an acid clay, such as that supplied by Filtrol Corporation of Los Angeles under the trade name Filtrol 20 which is an activated clay having acidity of 12 mg. KOH/gm.

The polymer product of this reaction is fractionated to remove lower molecular weight fractions which may ultimately contribute to lens cloudiness or biological interaction. Typically, as much as 40–60% of the polymer product is removed and the fractionated, high molecular weight product left forms component (a) in the compositions of this invention.

The crosslinker component (b) in the compositions of this invention is preferably a relatively high molecular weight polysiloxane containing crosslinkable groups and having at least one of the following general formulae (VIII), (VIIIA) and (VIIIB):

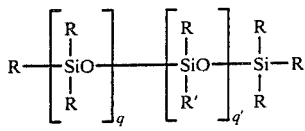

wherein the R substituents are the same or different and are as defined above, R' is as defined in Formula VI above, R' here being hydrogen when R' in Formula V is alkenyl, and vice versa; and q is an average number from about 1 to 50 times the value of q'; preferably q' is an average number of from about 3 to 20; the material of Formula VIII having an average degree of polymerization of from about 50 to 5,000, preferably about 200 to 1,000, the average value of q being determined by the difference in value between the degree of polymerization and the average value of q', as will be recognized by those skilled in the art.

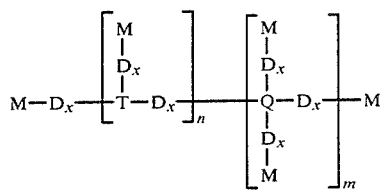

wherein
M is a monofunctional, silicon-containing, chain-capping residue which is free of crosslinkable groups;
D is a difunctional siloxane monomer unit;
T is a trifunctional siloxane monomer unit; and
Q is a tetrafunctional siloxane monomer unit; and wherein n and x are average positive numbers, m is 0 or an average positive number, the total of n+m being from about 2 to 100 and, when m=0, n alone has these values, the degree of polymerization (DP) being from 50 to 5,000. Therefore, in combination with the values of m and n given above, this degree of polymerization determines the values of x; and wherein M, D, T, and Q are as described above and the material of Formula VIIIA has, on average, from about 1 to 100 branch sites per molecule and, on average, from about 3 to 102—SiMe₂H groups per molecule, the material having an average degree of polymerization of from about 50 to 5,000;

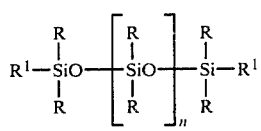

wherein R and R¹ are as defined above, n is an average number substantially equal to the average degree of polymerization of the material which is from about 50 to 5,000.

Component (b) is thus, on average, a relatively large molecule to counter crosslinker migration from the uncured and cured product. Since that product is fixed in the body it is not possible to remove small, migrateable components from the composition after cure. Therefore, unusually, the crosslinker (b) in the compositions of this invention is a macromolecule having a large molecular weight. Preferably also, the unreactive substituents on this molecule are similar to those on the polymer component (a) for compatibility and consequently clarity in the cured product.

The catalyst component (c) is a platinum compound of the type known for promoting crosslinking of these types of compositions. Preferably, the platinum is provided by chloroplatinic acid, preferably complexed with a siloxane such as tetramethylvinylcyclosiloxane (i.e., 1,3,5,7-tetramethyl-1,3,5,7-tetravinylcyclotetrasiloxane). The platinum catalyst is used in an amount to provide cure within about 24 hours of injection into the eye, preferably up to about 6 hours with lack of mobility occurring in about 1 to 2 hours after injection but allowing a pot life and injectability of the mixture of components (a), (b) and (c) of from about 1 to 6 hours after mixing. Nevertheless, the concentration of platinum should not be so great as to discolor the composition. Up to about 50 ppm of platinum may be used, preferably up to about 25 ppm.

Some preferred embodiments of this invention will now be more particularly described in and by the following examples, which also include comparative examples.

EXAMPLE 1

In preparation for making a silicone gel for use to form and cure intraocular lenses in situ, the following polymer was prepared: 245.1 g octamethylcyclotetrasiloxane (Me₂SiO)₄ Union Carbide Corp. A-40; 0.61 g 5 cs silicone fluid (Down Corning Corp. 5 cs 200 Fluid); 2.85 g 1,3,5,7-tetravinyl-1,3,5,7-tetramethylcyclotetrasiloxane, (MeViSiO)₄, (Union Carbide Corp.) and 0.0437 g KOH were loaded into a vessel, heated and given a nitrogen purge for about 4 hours at 150° C. Several gels were prepared in a manner similar to Example 4. All gels turned cloudy when allowed to rest in contact with saline or water at 36°–37° C.

EXAMPLE 2

In preparation for making a silicone gel for use to form and cure intraocular lenses in situ, the following polymer was prepared. 500 g hexamethylcyclotrisiloxane (Me₂SiO)₃ and 5.81 g 1,3,5-trivinyl-1,3,5-trimethylcyclotrisiloxane were loaded into a reaction flask with a mild nitrogen purge and stirring. The trimers were melted and 1.0 g Filtrol 20 acid clay (predried 1½ hours at 110° C.) was added when the trimers were at 72° C. Polymerization was complete in less than 30 minutes with an exotherm to 125° C. An extremely high molecular weight silicone polymer gum resulted. Clarity of this product was maintained in contact with water.

EXAMPLE 3

A copolymer of methylhydrogenpolysiloxane and dimethylpolysiloxane was prepared by loading 34.8 g Filtrol 20 (acid clay) and 700 ml toluene into a 3000 ml reaction flask filled with a means for stirring, a Dean Stark trap, and a condenser. Water was removed over a period of 16 hours. Some of the excess toluene (472 ml) was also removed to reduce reaction volume.

45 g methylhydrogenpolysiloxane (Me$_3$SiO[MeHSiO]$_x$SiMe$_3$)—Dow Corning 1107 fluid and 517.3 g octomethylcyclotetrasiloxane, (Me$_2$SiO)$_4$—Union Carbide Corp. A-40 was added to the flask. Sufficient additional toluene was removed so the boiling point of the mixture reached 138° C. Heating was continued up to 148° C. for an additional 5 hours. Filter aid and activated carbon were added after cooling and the product was filtered. The resultant polymer was stripped to 99.33% solids and active hydrogen content was determined to be 0.107% (bonded directly to silicon atoms).

EXAMPLE 4

A two component gel formulation was prepared in the following manner: the silicone polymer gum of example 2 was diluted in 1,1,1-trichloroethane to 5.4% solids and filtered. Fifteen (15) grams of this polymer gum (279.55 g solution) were added to 85 g silicone fluid that had a viscosity of 1000 centistokes. The 1,1,1,-trichloroethane was evaporated and the polymer blend (A) formulated as follows:
Part A:
 15 g polymer blend A as described above.
 0.54 g polymer of Example 2.
 This sample was thoroughly mixed with a spatula.
Part B:
 15 g polymer blend (A) as described above.
 0.36 g platinum complex similar to Petrarch Systems, Inc. Product PC085, except 0.25% platinum.

This sample was mixed thoroughly with a spatula. Each component was loaded into glass vials (2 g each) and sterilized 5 hours at 290° F. (143° C.). Part A and Part B were mixed 2 g each, de-aired and loaded into a sterile Luer-lok syringe fitted with a 19-gauge blunt needle. The lens of a rabbit was removed from its capsule using a dual needle technique with ultrasonic fragmentation of the lens. The mixed silicone was injected into the capsule and allowed to cure in place at body temperature. A second mix was allowed to cure at room temperature and showed gelation within 16 hours. After 3 weeks at 37° C. the cure appeared complete; however, very significant oiling of the cured gel had occurred and silicone apparently caused highly increased ocular pressure. A sample of the gel cured over saline remained very clear. Soxhlet extraction with xylene of the mix that had been cured at 36°–37° C. gave values of about 85% extractables.

EXAMPLE 5

A silicone polymer containing trimethylsiloxane end groups, branching sites of monomethylsiloxane, methylvinylsiloxane and a bulk of dimethylsiloxane was prepared by loading 477.8 g octamethylcyclotetrasiloxane, (Me$_2$SiO)$_4$ (Union Carbide Corp.); 16.88 g 5 centistoke silicone fluid (Dow Corning 5 cs 200 fluid); 8.5 g methyltriacetoxysilane, MeSi(OAc)$_3$ (Petrarch Systems, Inc.); 2.25 g 1,3,5,7-tetramethyl tetravinylcyclotetrasiloxane (Union Carbide) and 30 g Filtrol 20 (acid clay—Filtrol Corp. Los Angeles) into a reaction flask fitted with an electric heating mantle, means for stirring, and a water cooled reflux condenser. The ingredients were heated for about 2 hours at temperatures to 90° C. to allow initial equilibration of the siloxanes. The mixture was cooled and a Dean Stark trap was installed between the reaction flask and the condenser. Heating was continued to remove water (and acetic acid) from the flask for about 5 hours at temperatures to 125° C. A nitrogen purge of about 10 cubic feet per hour was used to assist volatile removal. At this point the trap was removed but the nitrogen purge was continued along with heating to 170° C. for an additional 7½ hours. Gel permeation chromatography indicated M$_n$ 18006, M$_z$ 1,239,720 and a polydispersity of 10.54. The resultant polymer was purified by extraction of the smaller molecules with isopropyl alcohol in 5 washes. The alcohol was warmed in the last two washes to solubilize higher molecular weight molecules. Approximately 37% of the polymer remained after the purification.

EXAMPLE 6

A two component gel was prepared by mixing 10 g of the purified polymer of Example 5 with 0.22 g of a platinum complex with 0.25% pt. content and labeled Component A. A second component B was prepared by mixing 15 grams of the purified polymer of Example 5 with 3.9 g of the crosslinker of Example 3. The separate components were final filtered with Celite 512 into separate 1 cc glass insulin syringes about 0.7 ml component in each syringe. Each syringe was heat sealed inside a sterilization pouch—and sterilized for 5 hours at 290° F. (145° C.). The syringes were fitted to the opposing parts of a 4-way stopcock and one empty two ml syringe was filtered to the remaining port. The valve was adjusted so material could flow from the two syringes containing Component A and Component B into the empty syringe. Equal portions of the two components were continuously injected into the 2 ml syringe. The valve was adjusted to one of the original syringes and the material passed back into it. Air bubbles were removed by adjusting the flow to the other report as they were encountered. The material was then mixed 15 cycles between the two syringes for a complete mixing. The resultant material cured in the presence of water at 35° C. in about six hours. A second mix was used to test for cell growth inhibition and none was found even at the 4-gram level as reported hereafter. Several additional mixes were injected into the evacuated lens capsules of rabbits. Excellent results were obtained in regard to inflammation and tissue reaction over a period of one to six months. In some cases, clarity and total appearance could not be distinguished from the unoperated eye. Soxhlet extraction with Xylene of the mix that had been cured ten days at 36°–37° C. gave values of about 45% extracted.

The two component gel of Example 6 was tested for cell growth inhibition and cytotoxicity as follows:

Cell Growth Inhibition

Sample was received for the determination of percent of cell growth inhibition. Nine sample weights were extracted in distilled water in the following ratios: 4000 milligrams (mg)/20 milliliters (ml), 500 mg/20 ml, 100 mg/20 ml, 50 mg/20 ml, 4 mg/20 ml, 3 mg/20 ml, 2 mg/20 ml, 1 mg/20 ml, 1 mg/40 ml. Sample was extracted at 121° C. for one hour.

For each extract, fifteen ml of each extract was aseptically added to fifteen ml of double strength Minimal Essential Medium (2×MEM) in a sterile container. Two ml of the test extract containing 2×MEM were added to each of ten assay tubes containing 0.2 ml of L 929 Mouse Fibroblast cells which were previously adjusted to $10^6$ cells/ml. The suspension in each of the ten assay tubes was then mixed. Ten additional tubes were prepared similarly as controls, substituting distilled water for sample extract solution. Half of the extract treated tubes were immediately incubated at 37° C. for 72 hours. The remaining tubes were centrifuged and the medium decanted. The cells were resuspended in sterile Phosphate Buffered Saline (PBS), centrifuged and the PBS decanted. The cells were resuspended, centrifuged and decanted twice again then stored for 72 hours at 4° C. At the end of the incubation period, the tubes at 37° C. were washed in the same manner as the refrigerated tubes. All tubes were assayed for protein content using a phenol reagent and measuring the degree of color development with the aid of a spectrophotometer. The average Optical Density (O.D.) of each set of five replicate tubes was determined and the percent of inhibition of cell growth was calculated as follows:

$$\% ICG = 100 - 100 \times \frac{(A) - (B)}{(C) - (D)}$$

where
A = Avg. O.D. 72 hour treated tubes,
B = Avg. O.D. zero time treated tubes,
C = Avg. O.D. 72 hours control tubes,
D = Avg. O.D. zero time control tubes.
The results were as follows:

| Extract | | Percent of Cell Growth Inhibition |
|---|---|---|
| 1. | 4,000 mg/20 ml | 4.6 |
| 2. | 500 mg/20 ml | 0 |
| 3. | 100 mg/20 ml | 2.7 |
| 4. | 50 mg/20 ml | 2.3 |
| 5. | 4 mg/20 ml | 1.0 |
| 6. | 3 mg/20 ml | 0.1 |
| 7. | 2 mg/20 ml | 2.3 |
| 8. | 1 mg/20 ml | 0.2 |
| 9. | 1 mg/40 ml | 0 |

It is concluded that the values expected for a non-toxic biomaterial in the nine point percent ICG Assay would fall below 10% inhibition. Values of 10–15% are suggestive of a low level inhibition. Values over 15% are considered positive evidence of cell growth inhibition. Under the conditions of this study all of the sample extracts fall below 10% ICG and, therefore do not produce cell growth inhibition.

Cytotoxicity

A monolayer of L-929 Mouse Fibroblast cells was grown to confluency and exposed to an extract of the test sample prepared by placing the sample material in 20 ml of Minimum Essential Medium (Eagle) and bovine serum (5%) and extracting at 37° C. for 24 hours. An MEM aliquot was used as a negative control. After exposure to the extract, the cells were examined microscopically for cytotoxic effect (CTE) and it was concluded that the sample was non-toxic.

EXAMPLE 7-15

The polymer of Example 5 can be represented with a general structural formula using the well known M, D, T, Q shorthand systems for silicone structures where $M = R_3SiO_{\frac{1}{2}}$; $D = R_2SiO$; $T = RSiO_{3/2}$ and $Q = SiO_{4/2}$. The average structure of the polymer of Example 5 is:

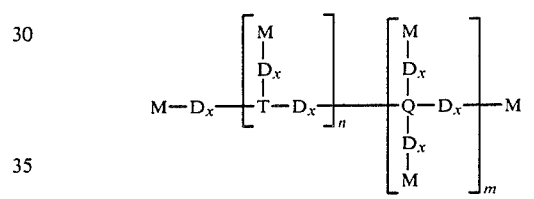

where
$M = Me_3SiO_{\frac{1}{2}}$; $D = D_1 + D_2$ where $D_1 = Me_2SiO$ and $D_2 = MeViSiO$; $T = MeSiO_{3/2}$; m = 0; x = 80 and n = 10.

The relative number of moles is therefore:
T = 11 moles,
M = 13 moles,
D = 80 + 160(10) + 2·80 = 1840,
Total Si = 1864.

The variation in R groups listed in Table I which follows has been demonstrated to give useful polymers with dangling ends when cured into gel. The general process of Example 5 was used except as noted.

TABLE I

| EXAMPLE | COMPONENT | MOLE RATIO | MONOMER USED | GRAMS | GPC $M_n$ | GPC $M_z$ | DISPERSITY |
|---|---|---|---|---|---|---|---|
| 5 | | | | | | | |
| n = 11 | $D_1$ | 1832.5/1864 | $(Me_2SiO)_4$ | 477.8 | 18006 | 1,239,720 | 10.54 |
| m = 0 | $D_2$ | 7.5/1864 | $(MeViSiO)_4$ | 2.25 | | | |
| x = 80 | M | 13/1864 | 5cs Silicone Fluid | 16.9 | | | |
| Si = 1864 | T | 11/1864 | $MeSi(OAc)_3$ | 8.5 | | | |
| 7 | | | | | | | |
| n = 11 | $D_1$ | 1840/1864 | $(Me_2SiO)_4$ | 483.5 | 19266 | 1,397,380 | 11.05 |
| m = 0 | $M_1$ | 9.3/1864 | 5cs silicone fluid | 12.18 | | | |
| x = 80 | $M_2$ | 3.7/1864 | $(ViMe_2Si)_2O$ | 1.23 | | | |
| Si = 1864 | T | 11/1864 | $MeSi(OAc)_3$ | 8.61 | | | |
| 8 | | | | | | | |
| n = 11 | $D_1$ | 1840/1864 | $(Me_2SiO)_4$ | 487.10 | 16463 | 1,518,420 | 15.08 |
| m = 0 | $M_1$ | 5.5/1864 | 5cs silicone fluid | 7.33 | | | |
| x = 80 | $M_2$ | 7.46/1864 | $(ViMe_2Si)_2O$ | 2.49 | | | |
| Si = 1864 | T | 3.9/1864 | $MeSi(OAc)_3$ | 3.07 | | | |
| 9¹ | | | | | | | |

TABLE I-continued

| EXAMPLE | COMPONENT | MOLE RATIO | MONOMER USED | GRAMS | GPC $M_n$ | GPC $M_z$ | DISPERSITY |
|---|---|---|---|---|---|---|---|
| n = 11 | $D_1$ | 115/1864 | $Me_2SiCl_2$ | 53.72 | 7609 | 102,096 | 3.92 |
| m = 0 | $D_2$ | 1725/1864 | $(Me_2SiO)_4$ | 414.9 | | | |
| x = 80 | M | 131/1864 | $Me_3SiCl$ | 5.12 | | | |
| Si = 1864 | T | 11/1864 | $ViSiCl_3$ | 6.33 | | | |
| | | | Acid Clay | 3 g | | | |
| $10^2$ | $D_1$ | 430/8690 | $Me_2SiCl_2$ | 43.122 | Very viscous polymer similar in character to Examples 5, 6, and 10 | | |
| n = 45 | $D_2$ | 8170/8690 | $(Me_2SiO)_4$ | 469.99 | | | |
| m = 0 | M | 46/8690 | $Me_3SiCl$ | 3.887 | | | |
| x = 945 | $T_1$ | 8/8690 | $ViSiCl_3$ | 1.004 | | | |
| Si = 8690 | $T_2$ | 36/8690 | $MeSiCl_3$ | 4.184 | | | |
| | | | Acid Clay | 10.0 g | | | |
| $11^2$ | $D_1$ | 2000/20,000 | $Me_2SiCl_2$ | 87.010 | 14,808 | 2,225,400 | — |
| n = 201 | $D_2$ | 17598/20,000 | $(Me_2SiO)_4$ | 439.80 | | | |
| m = 0 | M | 202/20,000 | $Me_3SiCl$ | 7.397 | | | |
| x = 48.6 | $T_1$ | 40/20,000 | $ViSiCl_3$ | 2.178 | | | |
| Si = 20,000 | $T_2$ | 160/20,000 | $MeSiCl_3$ | 8.063 | | | |
| | | | Acid Clay | 10.0 g | | | |
| $12^2$ | | | | | | | |
| n = 44 | D | 4892/5000 | $(Me_2SiO)_4$ | 469.54 | 19736 | 3,634,070 | 14.15 |
| m = 0 | M | 55/5000 | 5cs silicone fluid | 26.36 | | | |
| x = 50 | $T_1$ | 10/5000 | $ViSi(OAc)_3$ | 3.01 | | | |
| Si = 5000 | $T_2$ | 43/5000 | $(MeHSiO)_n$ | 3.39 | | | |
| 13 | | | | | | | |
| n = 11 | D | 1840/1864 | $(Me_2SiO)_4$ | 480.28 | 50754 | 4,980,280 | 7.88 |
| m = 0 | M | 13/1864 | 5cs silicone fluid | 16.97 | | | |
| x = 80 | $T_1$ | 3.7/1864 | $ViSi(OAc)_2$ | 3.05 | | | |
| Si = 1864 | $T_2$ | 7.3/1864 | $MeSi(OAc)_3$ | 5.65 | | | |
| 14 | | | | | | | |
| n = 11 | D | 1837.1/1864 | $(Me_2SiO)_4$ | 479.1 | 21724 | 5,887,520 | 20.11 |
| m = 0 | $D_2$ | 2.9/1864 | $(MeViSiO)_4$ | 0.88 | | | |
| x = 80 | M | 13/1864 | 5cs silicone fluid | 16.92 | | | |
| Si = 1564 | T | 11/1864 | $MeSi(OAc)_3$ | 8.53 | | | |
| 15 | | | | | | | |
| n = 21 | D | 5150/5253 | $Me_2SiO$ | 467.87 | A viscous polymer was obtained | | |
| m = 20 | M | 63/5253 | 5cs silicone fluid | 28.617 | | | |
| x = 50 | T | 21/5253 | $ViS(OAc)_3$ | 5.989 | | | |
| Si = 5253 | Q | 20/5253 | $SiO(Ac)_4$ | 6.482 | | | |

[1] In Example 9 the chlorosilanes were first dissolved in 65 g 1,1,1-Trichloroethane. 10 g $H_2O$ in 22 g acetone was added slowly to hydrolize the chlorosilane. The hydrolyzate was then condensed with acid clay (3 g) over 16 hrs. @ 80–115° C. with a $N_2$ purge.
[2] Process similar to Example 9.

I claim:

1. A method of replacing the lens in the eye of a human being or other animal in vivo which comprises:
   introducing into the lens capsule, from which the natural lens has been removed, a curable liquid polymer composition comprising crosslinkable polymer and crosslinker through a needle inserted into a hole in the lens capsule;
   sealing the hole in the lens capsule by curing the polymer composition that is in the vicinity of the hole to an extent sufficient to prevent loss of said composition from the lens capsule prior to withdrawing the needle from the hole; and
   curing said composition to form in situ a clear, synthetic lens.

2. The method of claim 1, wherein the sealing step includes heating the composition in the vicinity of the hole to effect localized curing of the composition.

3. The method of claim 1, in which the sealing step further includes cauterizing the hole.

* * * * *